United States Patent
Kamen

[19]

[11] Patent Number: 6,110,143
[45] Date of Patent: Aug. 29, 2000

[54] INFLATION/DEFLATION MEDICAL DEVICE

[76] Inventor: Jack M. Kamen, 8782 N. Cricket Tree La., Indianapolis, Ind. 46260

[21] Appl. No.: 09/104,707

[22] Filed: Jun. 25, 1998

[51] Int. Cl.⁷ .................................................. A61M 29/00
[52] U.S. Cl. .................................. 604/97.02; 128/207.15; 604/99.01
[58] Field of Search ........................... 604/97–100, 97.01, 604/97.02, 99.01, 99.02; 128/207.14–207.16

[56] References Cited

U.S. PATENT DOCUMENTS

| | | |
|---|---|---|
| 778,879 | 1/1905 | Molinari . |
| 1,343,085 | 6/1920 | Lerch . |
| 1,559,978 | 11/1925 | Page . |
| 2,474,496 | 6/1949 | Rayman . |
| 3,889,685 | 6/1975 | Miller, Jr. et al. . |
| 4,466,426 | 8/1984 | Blackman . |
| 4,509,514 | 4/1985 | Brain . |
| 4,642,102 | 2/1987 | Ohmori . |
| 4,795,431 | 1/1989 | Walling ..................................... 604/97 |
| 4,995,388 | 2/1991 | Brain . |
| 5,009,639 | 4/1991 | Keymling . |
| 5,038,766 | 8/1991 | Parker . |
| 5,042,469 | 8/1991 | Augustine . |
| 5,196,017 | 3/1993 | Silva et al. ................................ 604/97 |
| 5,203,320 | 4/1993 | Augustine . |
| 5,241,956 | 9/1993 | Brain . |
| 5,297,547 | 3/1994 | Brain . |
| 5,305,743 | 4/1994 | Brain . |
| 5,328,486 | 7/1994 | Woodruff . |
| 5,339,805 | 8/1994 | Parker . |
| 5,355,879 | 10/1994 | Brain . |
| 5,376,081 | 12/1994 | Sapienza . |
| 5,477,851 | 12/1995 | Callaghan et al. . |
| 5,487,731 | 1/1996 | Denton . |
| 5,513,627 | 5/1996 | Flam . |
| 5,591,130 | 1/1997 | Denton . |
| 5,632,271 | 5/1997 | Brain . |
| 5,653,690 | 8/1997 | Booth et al. . |

FOREIGN PATENT DOCUMENTS

| | | |
|---|---|---|
| 0 294 200 A2 | 12/1988 | European Pat. Off. . |
| 0 294 200 B1 | 12/1988 | European Pat. Off. . |
| 0 448 878 A2 | 10/1991 | European Pat. Off. . |
| WO 95/33506 | 12/1995 | WIPO . |
| WO 97/12640 | 4/1997 | WIPO . |

OTHER PUBLICATIONS

Instruction Video—Intavent Laryngeal Mask Airway.
Instruction Manual—The Intavent Laryngeal Mask, Oct. 1992.
Instruction Manual—Laryngeal Mask LMA®Airway, Aug. 1996.
Brochure—Laryngeal LMA®Mask Airway.

Primary Examiner—Corrine McDermott
Attorney, Agent, or Firm—Bose McKinney & Evans LLP

[57] ABSTRACT

A medical device is provided for substantially sealing a surface of a patient such as a surface defining a patient's air passage. The device includes a pliable body for sealing the surface of the patient and a pressure generation device for inflating and deflating the pliable body from an ambient position. The device further includes a valve configured to permit air to enter the pliable body after the device has been deflated to return the pliable body to the ambient position. After returning to the ambient position, the pressure generation device inflates the pliable body to an expanded position.

38 Claims, 5 Drawing Sheets

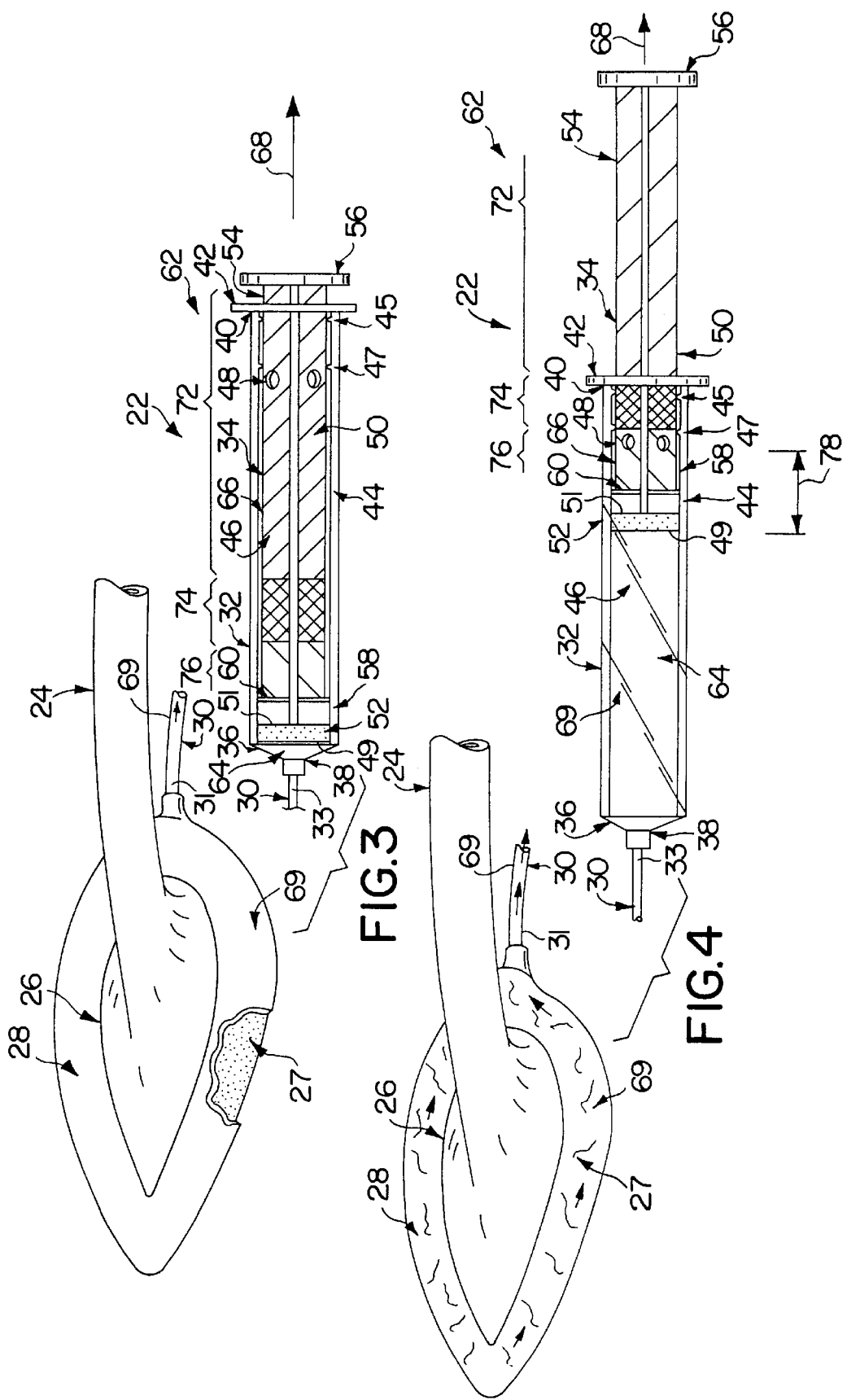

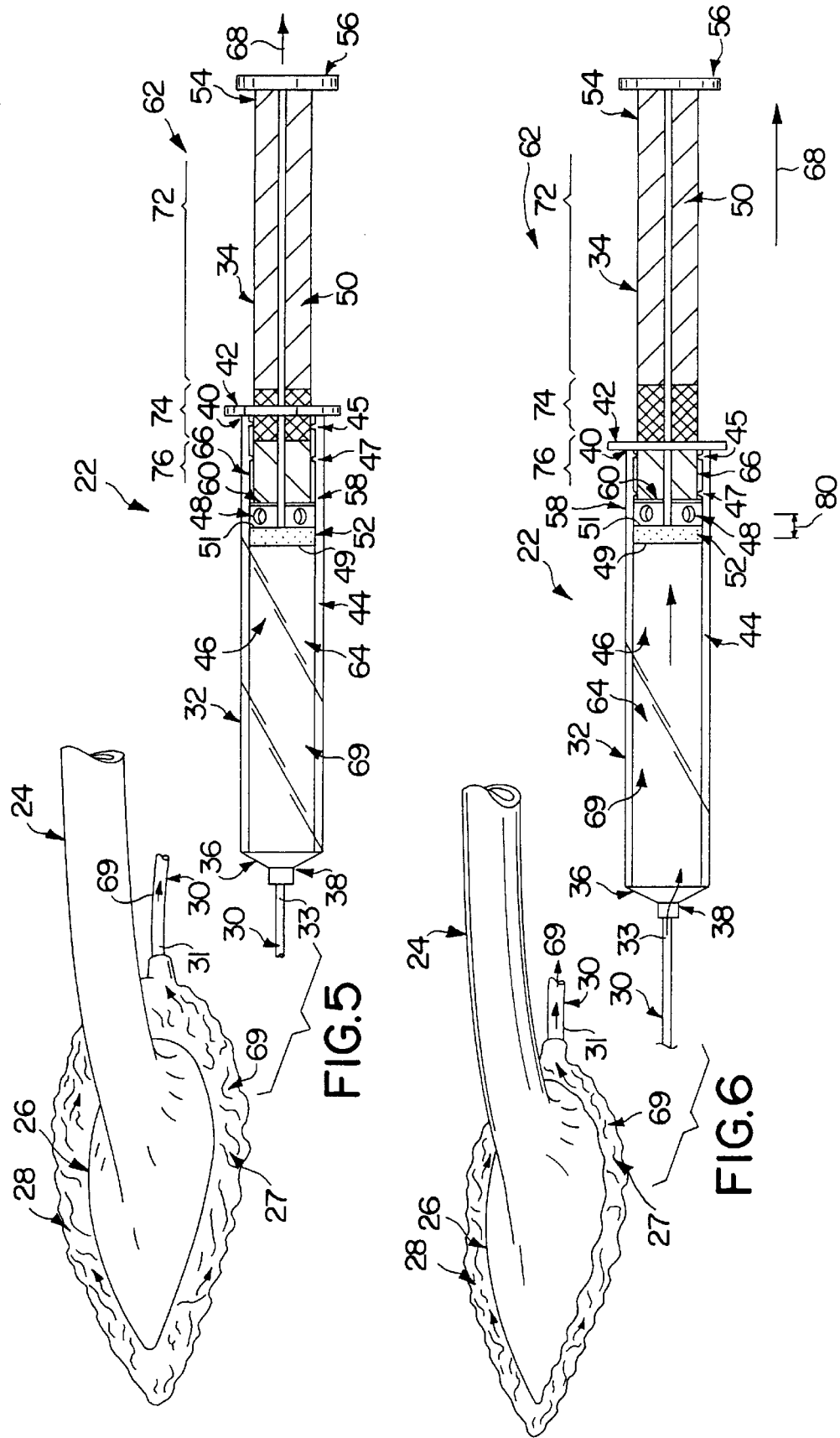

INFLATION/DEFLATION MEDICAL DEVICE

BACKGROUND AND SUMMARY OF THE INVENTION

The present invention relates to a medical device for deflating and inflating a body used for substantially sealing a surface. More particularly, this invention relates to a medical device including a pressure generation device used to deflate and inflate the body.

Medical personnel often use medical devices known as artificial airways for airway management in an effort to monitor and control gas and vapor flow to and from the patient's lungs. Artificial airways can be connected to the patient's airway in various locations and with various mechanisms. Some artificial airways use a pliable body that is inserted into the patient's airway and inflated to form a substantial seal with the patient's airway.

To initially place the pliable body in the patient's airway, it is often necessary to deflate the pliable body and reduce its volume. The pliable body is deflated by providing negative pressure to the interior of the pliable body. This reduction in volume makes the pliable body smaller and easier to insert into the patient's airway. After positioning the pliable body, the pliable body is then inflated by either relieving the negative pressure and allowing the pliable body to return to its ambient position or by applying positive pressure to the interior of the pliable body and expanding it beyond the ambient position.

According to the present invention, a pressure apparatus is provided for deflating and inflating a pliable body. The pressure apparatus includes a pressure generation device and a valve that communicates with a fluid region.

In a preferred embodiment, the pressure generation device includes a syringe having a barrel and a plunger. The barrel defines a chamber and includes a tip end, an open end spaced apart from the tip end, and a wall extending between the tip end and open end. The wall of the barrel includes an aperture. The plunger is positioned to lie within the chamber defined by the barrel and includes a body portion and a seal portion.

The seal portion of the plunger is movable from a first seal position near the tip end of the barrel with the pliable body in a first pliable body position having a first volume to a second seal position between the tip end of the barrel and the aperture of the wall with the pliable body in a second pliable body position having a second volume less than the first volume. The seal portion is then movable to a third seal position between the aperture and the open end of the barrel which allows air to pass through the aperture, barrel, a conduit extending between the syringe and pliable body, and pliable body with the pliable body in a third pliable body position having a third volume that is greater than the second volume.

The seal portion of the plunger and the aperture in the wall function as a valve that allows air to enter the pliable body and relieves the negative pressure in the interior of the pliable body. Thus, the present invention provides a valve or a valve function that allows a doctor or other medical worker to relieve the negative pressure in the interior of the pliable body. By releasing the negative pressure, the pliable body inflates to its natural or ambient position to substantially seal the patient's airway.

Furthermore, by using the valve, the plunger of the syringe is in a position to provide positive pressure without having to remove the syringe from the conduit.

Additional features of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 3 is a perspective view of the cuff of the laryngeal mask airway, with portions cut away, and a side elevation view of the syringe showing the cuff in an ambient position and the corresponding position of the syringe, the syringe including a barrel and a plunger, the barrel having a tip end, an open end spaced apart from the tip end, a wall extending between the tip end and open end, and a plurality of apertures in the wall, the plunger having a seal portion and a body portion including an indicia having first, second, and third portions, the plunger being positioned to lie in the barrel in a first position with the seal portion of the plunger positioned to lie near the tip end of the barrel with only the first portion of the indicia exposed from the barrel indicating a pressure-generating position;

FIG. 4 is a perspective view of the cuff of the laryngeal mask airway and a side elevation view of the syringe showing the cuff in a partially deflated position and the corresponding position of the syringe after the plunger has moved from the first position shown in FIG. 3, the plunger being in a second position with the seal portion of the plunger positioned to lie between the tip end of the barrel and the apertures of the barrel creating a vacuum that draws air though the pilot tube to move the cuff to the partially deflated position with only the first portion of the indicia exposed from the barrel indicating the pressure-generating position;

FIG. 5 is a perspective view of the cuff of the laryngeal mask airway and a side elevation view of the syringe showing the cuff in another partially deflated position and the corresponding position of the syringe after the plunger has moved from the second position shown in FIG. 4, the plunger being in a third position with the seal portion of the plunger positioned to lie between the tip end of the barrel and the apertures of the barrel continuing to create a vacuum that draws air though the pilot tube to move the cuff to the partially deflated position, the second portion of the indicia being exposed from the barrel indicating a caution position.

FIG. 6 is a perspective view of the cuff of the laryngeal mask airway and a side elevation view of the syringe showing the cuff in a deflated position and the plunger in a corresponding position after the plunger has moved from the third position shown in FIG. 5, the plunger being in a fourth position with the seal portion of the plunger positioned to lie between the tip end of the barrel and the apertures of the barrel near the apertures and continuing to create a vacuum that draws air through the pilot tube and moves the cuff to the deflated position, the third portion of the indicia being exposed indicating a trigger position;

DETAILED DESCRIPTION OF THE DRAWINGS

Figure 1:
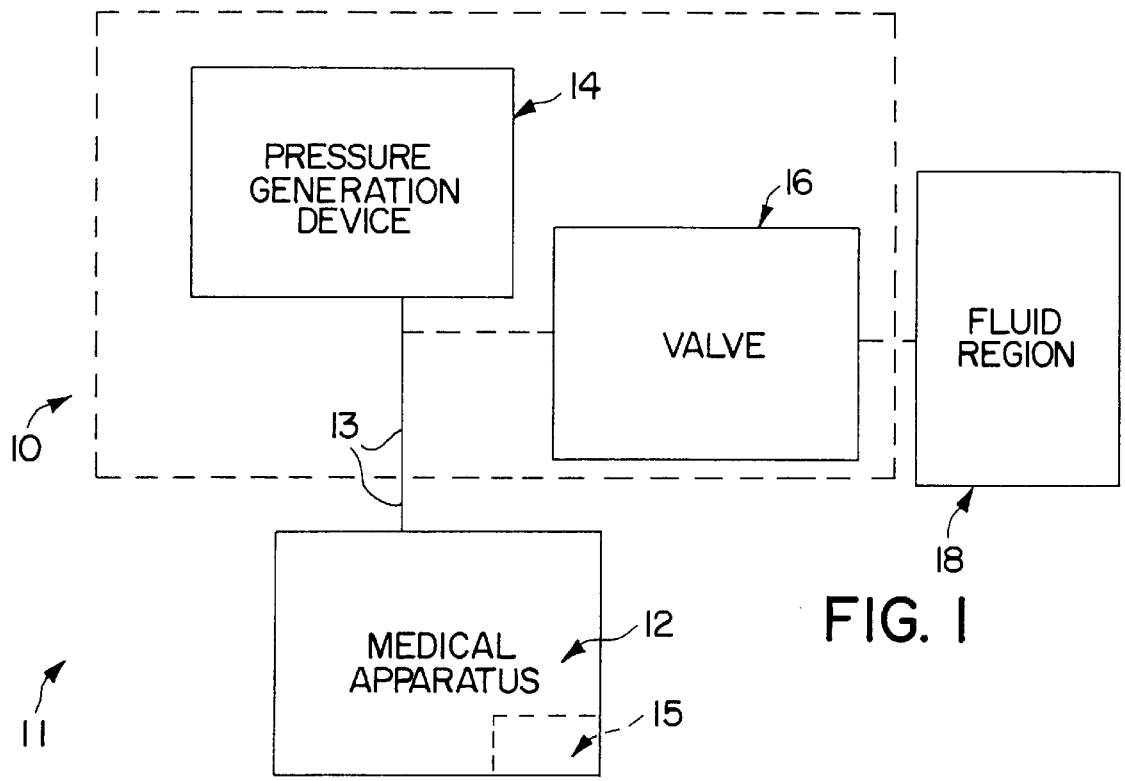
FIG. 1 is a diagrammatic view of a medical device showing the medical device including a pressure apparatus, the pressure apparatus including a pressure generation device and a valve in fluid communication with the pressure generation device and a fluid region, the pressure apparatus being in fluid communication with a medical apparatus.

A medical device 11 is provided including a pressure apparatus 10 in fluid communication with a medical apparatus 12 as shown in FIG. 1. Pressure apparatus 10 is provided to enable a doctor or other medical worker to control the deflation and inflation of a pliable body 15 of medical apparatus 12. The pliable body is used for substantially sealing a surface (not shown). Pressure apparatus 10 includes a pressure generator or pressure generation device 14 in fluid communication with pliable body 15 of medical apparatus 12 for creating negative or positive pressure in pliable body 15 and a valve 16 in fluid communication with pliable body 15 and a fluid region 18.

Pliable body 15 and pressure apparatus 10 cooperate to define an interior region or fluid system 13 that permits fluid communication between pressure apparatus 10 and pliable body 15. Valve 16 separates fluid region 18 from fluid system 13 and controls the introduction of a fluid, such as air, from fluid region 18, such as the atmosphere, to fluid system 13 to permit the inflation of pliable body 15 while pressure apparatus 10 is in fluid communication with the remainder of fluid system 13.

In the illustrated embodiment of FIGS. 2–8, medical apparatus 12 is a laryngeal mask airway 20, pressure generation device 14 and valve 16 are a syringe 22, and fluid region 18 is the atmosphere. Laryngeal mask airway 20 is used to substantially seal a surface over the patient's laryngeal opening. Laryngeal mask airway 20 includes a catheter 24 defining a passageway for air and other gasses and vapors to travel through laryngeal mask airway 20, a mask 26 including a cuff 28 for substantially sealing a surface over the laryngeal opening, and a conduit or pilot tube 30 in fluid communication with cuff 28 and syringe 22 for fluid communication therebetween. Pilot tube 30 includes a first end 31 coupled to cuff 28 and a second end 33 spaced apart from first end 31 and coupled to syringe 22. An example of a laryngeal mask airway is disclosed in U.S. Pat. No. 5,988,167, entitled FOAM CUFF FOR LARYNGEAL MASK AIRWAY and filed May 2, 1997 by Jack M. Kamen which is incorporated herein by reference. In alternative embodiments, the medical apparatus may be other devices including, but not limited to, endotracheal tubes with balloon cuffs and cuffed oropharyngeal airways.

In the illustrated embodiment, pliable body 15 of medical apparatus 12 is cuff 28. Cuff 28 can be deflated or expanded when an interior region 27 of cuff 28 is exposed to negative or positive pressure, respectively, from syringe 22. Before insertion into the patient's airway, cuff 28 is deflated from an ambient position having a first volume, as shown in FIG. 3, to a deflated position, as shown in FIG. 6, having a second volume that is less than the first volume. Cuff 28 is deflated by creating negative pressure in syringe 22 which draws air from interior region 27 of cuff 28 through pilot tube 30.

Figures 7, 8:
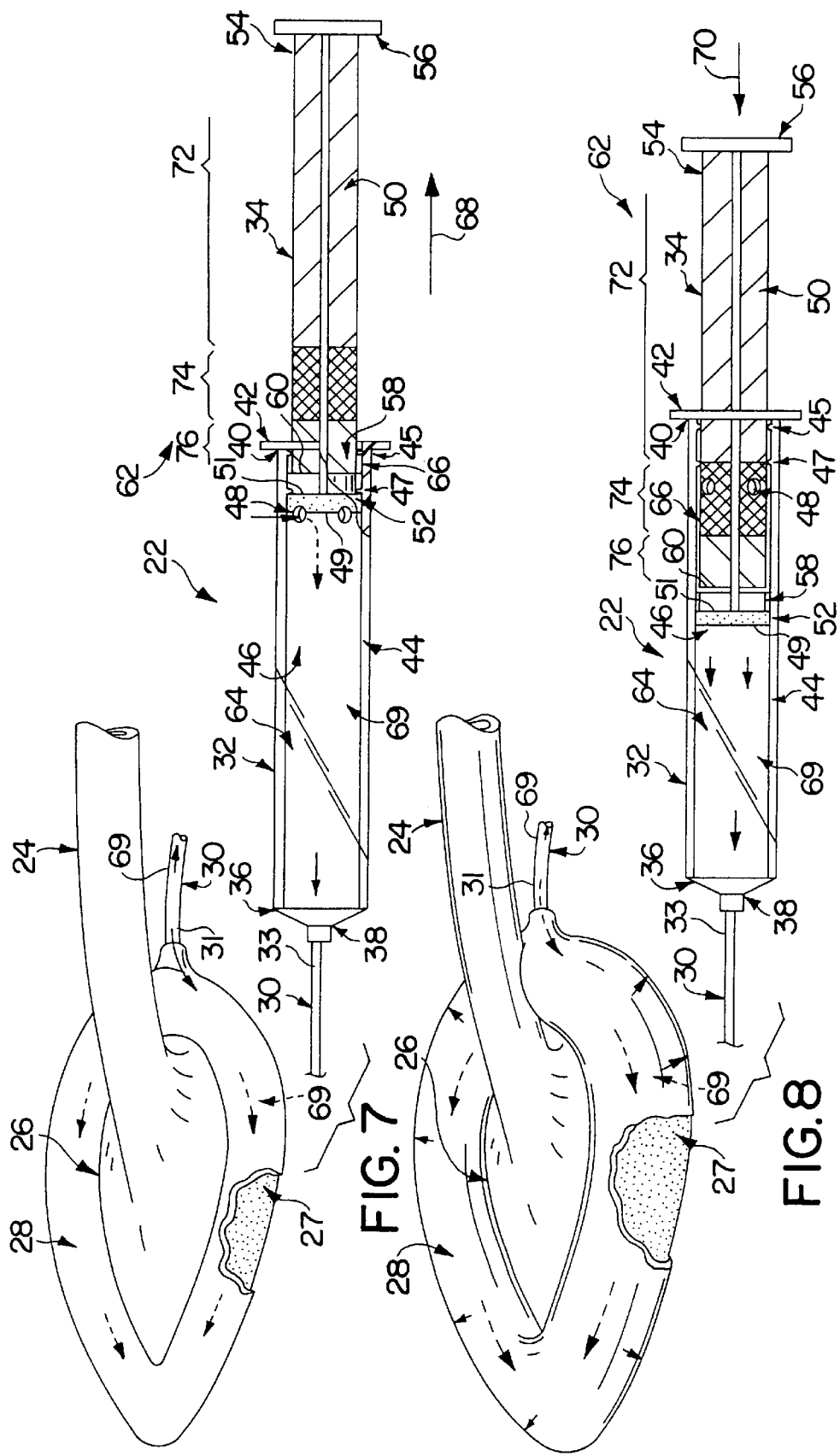
FIG. 7 is a perspective view of the cuff of the laryngeal mask airway, with portions cut away, and a side elevation view of the syringe showing the cuff in an inflated or ambient position and the corresponding position of the syringe after the plunger has moved from the fourth position shown in FIG. 6, the plunger being in a fifth position with a segment of the seal portion positioned to lie between the open end of the barrel and the apertures of the barrel permitting air to be drawn in from the atmosphere through the barrel and pilot tube to the cuff to move the cuff to the inflated position.
FIG. 8 is a perspective view of the cuff of the laryngeal mask airway, with portions cut away, and a side elevation view of the syringe showing the cuff in an expanded position and the corresponding position of the syringe after the plunger has moved from the fifth position shown in FIG. 7, the plunger being in a sixth position with the seal portion positioned to lie between the tip end of the barrel and the apertures of the barrel creating positive pressure that forces air through the pilot tube to move the cuff to the expanded position.

After cuff 28 is inserted into the patient's airway and positioned to lie over the patient's larynx, cuff 28 is inflated from the deflated position to an ambient or inflated position having a third volume as shown in FIG. 7. Cuff 28 is inflated by exposing interior region 27 of cuff 28 to atmospheric pressure that relieves the negative pressure and allows air to enter interior region 27 of cuff 28. If cuff 28 does not sufficiently seal the surface over the laryngeal opening, cuff 28 can be expanded from the ambient position to an expanded position as shown in FIG. 8. Cuff 28 is expanded by creating positive pressure in syringe 22 which forces air into cuff 28 through pilot tube 30.

As previously mentioned, syringe 22 is used to generate negative and positive pressure for the removal and addition of air to interior region 27 of cuff 28. Syringe 22 includes a barrel 32 and a plunger 34. Barrel 32 includes a tip end 36 having a nozzle 38 that is adapted to mate and communicate with pilot tube 30, an open end 40 having a collar 42, and a wall 44 extending between tip end 36 and open end 40. Wall 44 defines a chamber 46 and includes a first ridge 45, a second ridge 47 spaced apart from first ridge 45, and a plurality of apertures 48 in fluid communication with chamber 46 and the atmosphere.

Plunger 34 is positioned to lie in chamber 46 and includes a member or body portion 50 and a seal or seal portion 52 having a first side 49 and a second side 51 spaced apart from first side 49. Body portion 50 includes a handle end 54 having a first collar 56, a seal end 58 spaced apart from handle end 54 and having a second collar 60, and a plunger location indicia 62. Seal portion 52 is coupled to body portion 50 at seal end 58 of body portion 50 and defines a first portion 64 of chamber 46 positioned between seal portion 52 and tip end 36 of barrel 32 and a second portion 66 of chamber 46 positioned between seal portion 52 and open end 40.

Syringe 22 generates negative pressure by moving plunger 34 in direction 68 from a first plunger position, as shown in FIG. 3, to second, third, and fourth plunger positions as shown in FIGS. 4–6. As plunger 34 is moved in direction 68, seal portion 52 slides along and substantially seals against wall 44 of barrel 32. Because of this sealing, first portion 64 is substantially isolated from the atmosphere. Thus, movement of seal portion 52 in direction 68 increases the volume of first portion 64 of chamber 46 and creates negative pressure in first portion 64.

When syringe 22 is coupled to pilot tube 30, first portion 64 of chamber 46, pilot tube 30, and interior region 27 of cuff 28 define an air passageway or air system 69 that is substantially isolated from the atmosphere when seal portion 52 of plunger 34 is positioned to lie between tip end 36 of barrel 32 and apertures 48. Air system 69 provides fluid communication between syringe 22 and interior region 27 of cuff 28 and is an illustrated embodiment of fluid system 13. Because air system 69 provides fluid communication between syringe 22 and interior region 27 of cuff 28, the negative pressure in first portion 64 of chamber 46 draws air from interior region 27 of cuff 28 and transmits the negative pressure to interior region 27 of cuff 28. Because interior region 27 of cuff 28 is at a pressure level less than the atmosphere and is pliable, cuff 28 deflates. This deflation aids the doctor or medical worker in inserting laryngeal mask airway 20 into a patient's airway because cuff 28 has a reduced volume and size as shown in FIG. 6.

Figure 2:
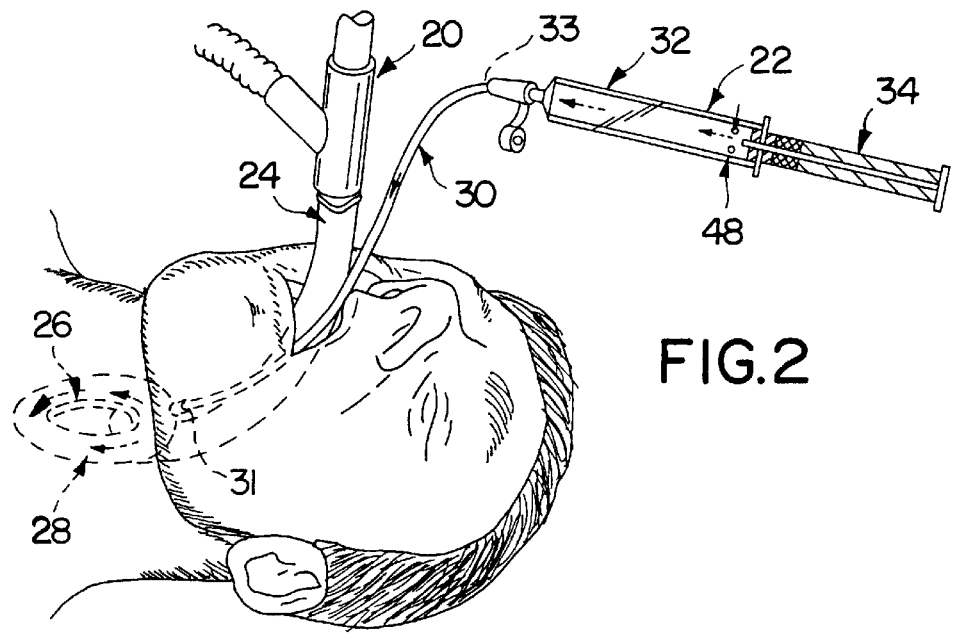
FIG. 2 is a perspective view of a patient showing a syringe as an illustrative embodiment of the pressure apparatus in fluid communication with a cuff of a laryngeal mask airway as an illustrative embodiment of the medical apparatus, the laryngeal mask airway including a tube coupled to the syringe and the cuff to provide fluid communication therebetween.

After insertion of laryngeal mask airway 20 into a patient's airway, cuff 28 is inflated so that cuff 28 is at the ambient position, as shown in FIGS. 2 and 7, and substantially seals over the patient's larynx. To inflate cuff 28 to the ambient position, the negative pressure in interior region 27 of cuff 28 is relieved by moving plunger 34 from the fourth plunger position, as shown in FIG. 6, to a fifth plunger position as shown in FIG. 7. As plunger 34 is moved to the fifth plunger position, first side 49 of seal portion 52 moves past a portion of apertures 48 and exposes first portion 64 of chamber 46 to the atmosphere.

The exposure of first portion 64 of chamber 46 to the atmosphere relieves the negative pressure in air system 69. As first portion 64 of chamber 46 is exposed to the atmosphere, the negative pressure draws air into air system 69 including interior region 27 of cuff 28 as shown in FIG. 7. The additional air inflates cuff 28 until it reaches the ambient position and substantially seals over the patient's larynx as shown in FIG. 2.

Apertures 48 of barrel 32 and seal portion 52 cooperate to perform as an illustrated embodiment of valve 16. When plunger 34 moves from the fourth plunger position to the fifth plunger position, first side 49 of seal portion 52 exposes first portion 64 of chamber 46 to the atmosphere through apertures 48. Thus, as first side 49 of seal portion 52 moves past a portion of apertures 48, first portion 64 of chamber 46 and the remainder of air system 69 change from being substantially isolated from the atmosphere to exposed to the atmosphere which allows air from the atmosphere into air system 69 including interior region 27 of cuff 28. Thus, apertures 48 and seal portion 52 function as a valve that controls the flow of air into first portion 64 of chamber 46 and the remainder of air system 69 from the atmosphere.

Apertures 48 of barrel 32 and seal portion 52 expose and substantially isolate air system 69 from the atmosphere while syringe 22 remains coupled to pilot tube 30. Therefore, to activate the valve function of apertures 48 and seal portion 52, syringe 22 does not need to be removed from pilot tube 30.

Valve 16 is not limited to being positioned on pressure apparatus 10 as illustrated by apertures 48 and seal portion 52 placed in syringe 22. In alternative embodiments, valve 16 may be positioned to lie anywhere so that valve 16 is in fluid communication with pliable body 15 of medical apparatus 12 and fluid region 18. When positioned to lie in such an arrangement, valve 16 can control the flow of fluids between fluid region 18 and pliable body 15 of medical apparatus 12.

On occasion, cuff 28 is moved from the ambient position, as shown in FIG. 7, to the expanded position, as shown in FIG. 8, to expand cuff 28 to provide a more substantial seal on a surface over the laryngeal opening. To expand cuff 28 to the expanded position, positive pressure is created in syringe 22 and communicated to interior region 27 of cuff 28 by moving plunger 34 in direction 70 from the fifth plunger position, as shown in FIG. 7, to a sixth plunger position as shown in FIG. 8. As plunger 34 is moved to the sixth plunger position, first side 49 of seal portion 52 moves past apertures 48 in direction 70 and substantially isolates first portion 64 of chamber 46 and the remainder of air system 69 from the atmosphere. As plunger 34 is moved in direction 70, seal portion 52 slides along and substantially seals against wall 44 of barrel 32. This movement of seal portion 52 in direction 70 decreases the volume of first portion 64 of chamber 46 and air system 69 and creates positive pressure in first portion 64 and the remainder of air system 69.

Because air system 69 provides fluid communication between syringe 22 and interior region 27 of cuff 28, the positive pressure in first portion 64 of chamber 46 forces air through pilot tube 30 to interior region 27 of cuff 28 and transmits the positive pressure to interior region 27 of cuff 28. Because interior region 27 of cuff 28 is at a pressure level greater than the atmosphere and is pliable, cuff 28 expands. This expansion of cuff 28 creates a more substantial seal on a surface over the laryngeal opening.

As previously mentioned, body portion 50 of plunger 34 includes indicia 62. Indicia 62 indicates the position of seal portion 52 relative to apertures 48 as plunger 34 is moved from the first plunger position to the fifth plunger position so that a doctor or other medical worker has an indication of how close they are to activating the valve function of apertures 48 and seal portion 52.

Indicia 62 includes first, second, and third portions 72, 74, 76 that are distinct from each other. When only first portion 72 is exposed from open end 40 of barrel 32, plunger 34 is in a pressure-generating position so that seal portion 52 is positioned to lie between tip end 36 and apertures 48 and spaced apart from apertures 48 by at least a distance 78, as shown in FIG. 4. Therefore, when plunger 34 is in the pressure-generating position, the doctor or other medical worker knows that seal portion 52 is substantially spaced apart from apertures 48 so that the doctor or other medical worker can generate either negative or positive pressure.

Exposure of second portion 74 of indicia 62 from open end 40 of barrel 32 indicates that seal portion 52 is nearing apertures 48 as shown in FIG. 5. Thus, as plunger 52 is moved in direction 68 from the second position as shown in FIG. 4, second portion 74 of indicia 62 is exposed from open end 40 of barrel 32 as shown in FIG. 5. While second portion 74 is exposed, plunger 34 is in a caution position so that seal portion 52 is spaced apart from apertures 48 by a distance less than distance 78 and the doctor or other medical worker is warned that seal portion 52 is nearing apertures 48 while generating additional pressure.

Exposure of third portion 76 of indicia 62 from open end 40 of barrel 32, as shown in FIG. 6, indicates that seal portion 52 is substantially adjacent apertures 48 so that slight movement of plunger 34 in direction 68 will expose first portion 64 of chamber 46 and the remainder of air system 69 to the atmosphere. Therefore, as plunger 52 is moved in direction 68 from the third position to the fourth position, third portion 76 of indicia 62 is exposed from open end 40 of barrel 32 as shown in FIG. 6. While third portion 76 is exposed, plunger 34 is in a trigger position so that seal portion 52 is substantially adjacent to apertures 48, as shown in FIG. 6, and a doctor or other medical worker needs to move plunger 34 slightly in direction 68 to expose first portion 64 of chamber 46 and the remainder of air system 69 to the atmosphere through apertures 48 as shown in FIG. 7. Thus, indicia 62 gives the doctor or other medical worker an indication of how close seal portion 52 is to apertures 48 and first portion 64 of chamber 46 is to being exposed to the atmosphere through apertures 48.

Interaction between second collar 60 of body portion 50 and second ridge 47 of wall 44 also indicates when seal portion 52 is positioned to lie substantially adjacent to apertures 48 and warns the doctor or other medical worker that slight movement of plunger 34 in direction 68 will expose first portion 64 of chamber 46 and the remainder of air system 69 to the atmosphere. As plunger 34 is moved in direction 68, second collar 60 of body portion 50 approaches and abuts second ridge 47 as shown in FIG. 6. When second collar 60 abuts second ridge 47, seal portion 52 is substantially adjacent to apertures 48. Because this abutment provides additional resistance, plunger 34 cannot be moved in direction 68 without additional effort by the doctor or other medical worker.

Because of the additional resistance provided by second ridge 47 and second collar 60, the doctor or other medical worker would have a tactile sensation of an increased resistance when seal portion 52 is substantially near apertures 48. This sensation warns the doctor or other medical worker that additional movement of plunger 34 in direction 68 will expose first portion 64 of chamber 46 and the remainder of air system 69 to the atmosphere through apertures 48. Therefore, to expose air system 69 to atmospheric relief, the doctor or other medical worker must exert additional effort to pull second collar 60 of body portion 50 past second ridge 47 in direction 68.

Figure 9:
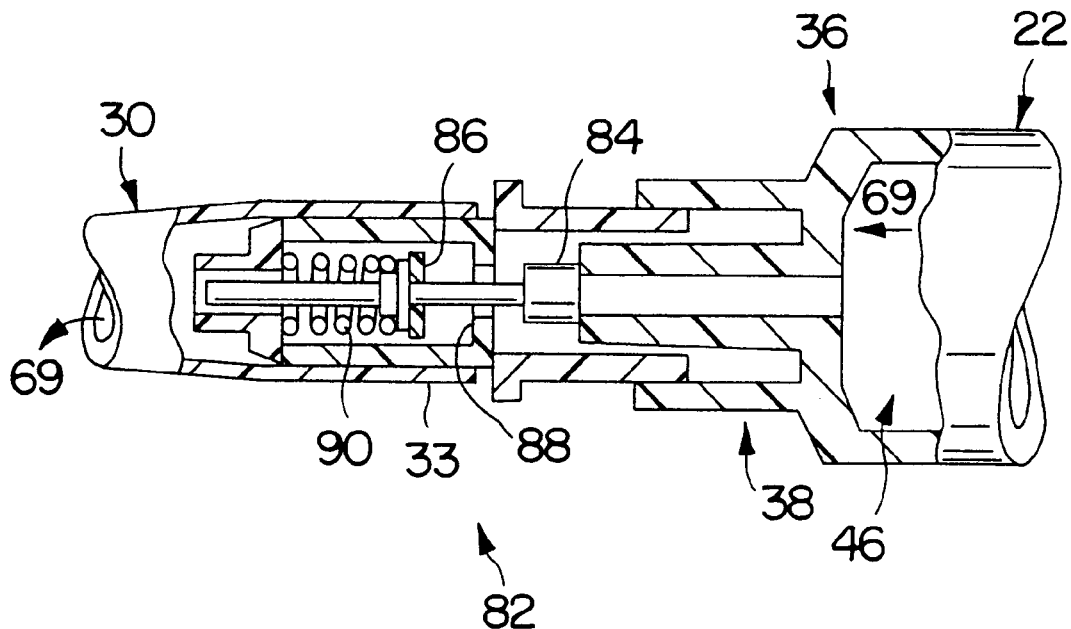
FIG. 9 is a side elevation view of the syringe and an alternative embodiment of the pilot tube, with portions cut away, showing the pilot tube including a valve and the syringe holding the valve in an open position when the syringe is coupled to the pilot tube.
Figure 10:
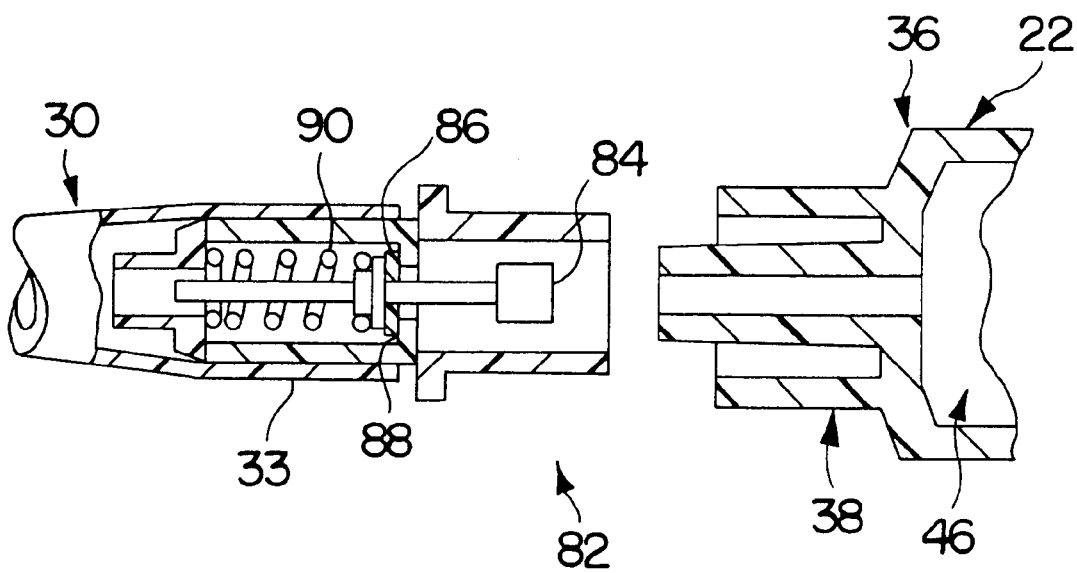
FIG. 10 is a side elevation view similar to FIG. 9 showing the valve in a closed position when the syringe is uncoupled from the pilot tube.

In an alternative embodiment of the present invention, a second valve 82 is positioned to lie in second end 33 of pilot tube 30 as shown, for example, in FIG. 9. Valve 82 controls the flow of air from syringe 22 to cuff 28 by closing or opening pilot tube 30. When syringe 22 is coupled to pilot tube 30, second valve 82 is in an open position because nozzle 38 depresses a button 84 on second valve 82 and moves a seal 86 away from a seal seat 88 against the bias of a spring 90 as shown in FIG. 9. When syringe 22 is removed from pilot tube 30, second valve 82 is in a closed position because nozzle 32 no longer depresses button 84 and spring 90 moves seal 86 against seal seat 88 substantially sealing pilot tube 30 and cuff 28 from the atmosphere as shown in FIG. 10.

In yet another embodiment of the present invention, apertures 48 are replaced by a single aperture (not shown) or apertures (not shown) of different sizes and shapes than apertures 48. Thus, any number, form, or type of apertures, openings, or valves that permit fluid communication between a chamber and the atmosphere may be used as valve 16.

Although this invention has been described in detail with reference to certain embodiments, variations and modifications exist within the scope and spirit of the invention as described and as defined in the following claims.

What is claimed is:

1. A medical device used to substantially seal a surface of a patient, the medical device comprising a syringe having a barrel and a plunger, the barrel including a tip end, an open end spaced apart from the tip end, and a wall extending between the tip end and open end, the barrel defining a chamber, the wall including an aperture, the plunger being positioned within the climber defined by the barrel, the plunger including a body portion and a seal portion, and a medical apparatus including a pliable body having a first inflated position with a first volume at ambient pressure, the barrel of the syringe being in fluid communication with the pliable body, the seal portion of the plunger being movable from a first seal position near the tip end of the barrel with the pliable body being in the first inflated position to a second seal position between the tip end of the barrel and the aperture of the wall with the pliable body being in a deflated position with a second volume substantially less than the first volume to a third seal position between the aperture and the open end of the barrel allowing a fluid to pass through the aperture, barrel, and pliable body with the pliable body being in a second inflated position having a third volume that is substantially greater than the second volume.

2. The medical device of claim 1, wherein in the seal portion of the plunger is movable from the third seal position to a fourth seal position between the tip end of the barrel and the aperture of the wall with the pliable body being in a fourth pliable body position having a fourth volume that is greater than the third volume.

3. A medical device for inflating and deflating a pliable body used to substantially seal a surface of a patient, the medical device comprising a syringe having a barrel and a plunger, the barrel including a tip end, an open end spaced apart from the tip end, and a wall extending between the tip end and open end, the barrel defining a chamber, the wall including an aperture, the plunger being positioned within the chamber defined by the barrel, the plunger including a body portion and a seal portion, and a conduit coupled to the syringe and the pliable body to provide fluid communication between the syringe and the pliable body, the seal portion of the plunger being movable from a first seal position near the tip end of the barrel with the pliable body being in a first pliable body position having a first volume to a second seal position between the tip end of the barrel and the aperture of the wall with the pliable body being in a second pliable body position having a second volume less than the first volume to a third seal position between the aperture and the open end of the barrel allowing a fluid to pass through the aperture, barrel, conduit, and pliable body with the pliable body being in a third pliable body position having a third volume that is greater than the second volume, the syringe including an indicia indicating the location of the seal portion of the plunger relative to the aperture of the wall of the barrel.

4. The medical device of claim 3, wherein the indicia includes first, second, and third portions, the first portion indicates that the seal portion of the plunger is spaced apart from the aperture of the wall of the barrel by at least a first distance, the second portion indicates that the seal portion of the plunger is spaced apart from the aperture by a second distance that is less than the first distance, and the third portion indicates that the seal portion of the plunger is substantially adjacent to the aperture.

5. A syringe in combination with a medical apparatus used to substantially seal a surface of a patient, the medical apparatus comprising a pliable body having a first pliable body position with a first pliable body width at ambient pressure, the syringe comprising
- a barrel having a tip end, an open end, and a wall extending between the tip end and open end, the wall including an aperture in fluid communication with the atmosphere, and the tip end being in fluid communication with the pliable body and
- a plunger positioned within the barrel and having a body portion and a seal portion, the seal portion being movable from a first position between the tip end and the aperture at a first distance from the aperture with the pliable body having the first pliable body width to a second position between the tip end and the aperture at a second distance from the aperture being less than the first distance with the pliable body having a second pliable body width substantially less than the first pliable body width to a third position between the aperture aid the open end allowing air to enter the aperture with the pliable body having a third pliable body width substantially different than the second pliable body width.

6. The syringe of claim 5, wherein the wall of the barrel includes a plurality of apertures.

7. A syringe for inflating and deflating a pliable body used to substantially seal a surface of a patient, the syringe comprising a barrel having a tip end, an open end, and a wall extending between the tip end and open end, the wall including an aperture in fluid communication with the atmosphere, and the tip end being adapted to be in fluid communication with the pliable body and
- a plunger having a body portion and a seal portion, the seal portion being movable from a first position between the tip end and the aperture at a first distance from the aperture with the pliable body having, a first pliable body volume to a second position between the tip end and the aperture at a second distance from the aperture being less than the first distance with the pliable body having a second pliable body volume different than the first pliable body volume to a third position between the aperture and the open end allowing air to enter the aperture with the pliable body having a third pliable body volume different than the second pliable body volume, the barrel including a ridge and the body portion of the plunger including a collar, the collar of the body portion abutting the ridge of the barrel when the seal portion of the plunger is substantially adjacent to the aperture in the wall of the barrel.

8. A medical device used to substantially seal a surface of a patient, the medical device comprising
- a body having an outer surface adapted to substantially seal the surface of the patient, an inner width, and an outer width defined by the outer surface, the outer width being substantially greater than the inner width when the body is at ambient pressure,
- a pressure generator in fluid communication with the body, the body and the pressure generator defining a fluid system, the pressure generator being operable to generate sub-ambient pressure in the fluid system to substantially reduce the outer width of the body to approximate the inner width of the body, and
- a valve being positioned at least partially outside the fluid system in a fluid region positioned outside of the fluid system the fluid region being at the ambient pressure, the valve controlling the flow of fluid between the fluid region and tie fluid system.

9. The medical device of claim 8, wherein the pressure generator is a syringe including a barrel and a plunger, the barrel includes a wall having an aperture, the plunger includes a body portion and a seal portion, the seal portion of the plunger and the aperture of the wall cooperate to define the valve.

10. The medical device of claim 8, wherein the medical device further includes a second valve positioned to lie in the fluid system and configured to control the flow of fluid through the fluid system.

11. The medical device of claim 8, wherein the valve is movable from a first position substantially sealing the fluid system from the fluid region to a second position exposing the fluid system to the fluid region while the pressure generator is in fluid communication with the body.

12. The medical device of claim 8, wherein the fluid region is the atmosphere and the fluid is air.

13. A medical device used to substantially seal a surface of a patient, the medical device comprising
- a body having an outer surface adapted to seal the surface of the patient and a support structure configured to support the outer surface at ambient pressure to define a volume therein,
- a pressure generator in fluid communication with the body, the body and the pressure generator defining a fluid system, the support structure being configured to collapse when sub-ambient pressure is applied to the body by the pressure generator, and
- a valve positioned between the body and a fluid region positioned outside of the fluid system while the pressure generator is in fluid communication with the body, the fluid region being at the ambient pressure, and the valve being configured to control the flow of fluid between the fluid region and the fluid system.

14. The medical device of claim 13, wherein the pressure generator includes a seal and an aperture, the seal and the aperture comprise the valve that is operable from an isolated position wherein the seal substantially seals the aperture from the fluid system to an exposed position wherein the aperture is in fluid communication with the fluid system and the fluid region and allows fluid to flow between the fluid system and the fluid region.

15. The medical device of claim 14, wherein the pressure generator includes a syringe having a barrel having a wall including the aperture and a plunger positioned in the barrel and including a body portion and a seal portion including the seal.

16. The medical device of claim 14, further comprising a second valve positioned to lie in the fluid system and configured to control the flow of fluid through the fluid system.

17. The medical device of claim 13, wherein the pressure generator is in fluid communication with the body while the valve controls the flow of fluid between the fluid region and the fluid system.

18. A medical device used to substantially seal a surface of a patient, the medical device comprising
- a body having an inflated position having an inflated width at ambient pressure,
- a pressure generation device in fluid communication with the body, the pressure generation device and the body defining a fluid system, the pressure generation device being operable to create sub-ambient pressure in the body to move the body to a deflated position having a deflated width substantially less than the inflated width to facilitate insertion of the body into the patient,
- a first valve in fluid communication with the fluid system and configured to control the flow of fluid through the fluid system, and a second valve in fluid communication with the fluid system and a fluid region positioned outside of the fluid system, the fluid region being at the ambient pressure and the second valve being configured to control the flow of fluid from the fluid region and into the fluid system to inflate the body.

19. The medical device of claim 18, wherein the pressure generation device is a syringe including a barrel and a plunger positioned within the barrel, the barrel includes a tip end, an open end spaced apart from the tip end, and a wall extending between the tip end and open end, and an aperture, the plunger includes a body portion and a seal portion, and the seal portion and the aperture define the second valve.

20. The medical device of claim 19, wherein the plunger is movable from a first position with the seal portion positioned to lie between the tip end of the barrel and the aperture with the seal portion substantially sealing the fluid system from the fluid region to a second position so the aperture exposes the fluid system to the fluid region.

21. A medical device used to substantially seal a surface of a patient, the medical device comprising
   a body having a volume,
   a pressure apparatus in fluid communication with the body, the pressure apparatus including a member defining a chamber and a valve in fluid communication with the chamber and a fluid region positioned outside of the fluid system, the fluid region being at the ambient pressure, the valve being operable from a first position substantially sealing a portion of the chamber from the fluid region to a second position exposing the portion of the chamber to the fluid region while the pressure apparatus is in fluid communication with the body to inflate the body from a deflated position having a deflated width to an inflated position having a inflated width substantially greater than the deflated width.

22. The medical device of claim 21, wherein the member is a barrel of a syringe and the valve includes a seal portion of a plunger included in the syringe and an aperture included in a wall of the barrel, the seal portion substantially seals the portion of the chamber from the fluid region while in a first position and is movable to a second position exposing the portion of the chamber to the fluid region.

23. The medical device of claim 21, wherein the valve is coupled to the member of the pressure apparatus.

24. A medical device used to substantially seal a surface of a patient, the medical device comprising
   a catheter having an outer width,
   a body having a volume,
   a pressure generation device,
   a conduit having a first end coupled to the body and a second end coupled to the pressure generation device, the pressure generation device being in fluid communication with the body through the conduit, and the body, the pressure generation device, and the conduit defining an interior region, and
   a valve coupled to one of the body, the pressure generation device, and the conduit, the valve being spaced apart from the second end of the conduit, the valve being operable from a first position substantially sealing the interior region From a fluid region positioned outside of the interior region to a second position exposing the interior region to the fluid region to permit fluid to flow into the interior region from the fluid region to inflate the body from a deflated position having a deflated width substantially equal to the outer width of the catheter to an inflated position having an inflated width substantially greater than the width of the catheter.

25. The medical device of claim 24, wherein the pressure generation device is a syringe.

26. The medical device of claim 25, wherein the syringe includes a barrel having a wall including an aperture and a plunger positioned within the barrel and having a body portion and a seal portion, the seal portion and aperture define the valve, the seal portion is operable from a first position relative to the aperture to substantially seal the interior region from the fluid region to a second position relative to the aperture to expose the interior region to the fluid region so that fluid may flow between the fluid region and the interior region.

27. A medical device used to substantially seal a surface of a patient passageway, the medical device comprising
   a body having an outer surface adapted to substantially seal the surface of the patient and a volume defined by the outer surface, and
   means for deflating tile body from an ambient position having a first width to a deflated position having a second width substantially less than the first width to facilitate insertion of the body into the patient passageway and for inflating the body from the deflated position to a position wherein the body has a third width substantially greater than the second width and substantially seals the surface of the patient while the deflating and inflating means remain in fluid communication with the body.

28. The medical device of claim 27 wherein the deflating means includes a syringe.

29. The medical device of claim 28, wherein the syringe includes a barrel including an aperture providing the inflating means.

30. The medical device of claim 29, wherein the syringe further includes a plunger positioned in the barrel and having a seal portion and the syringe includes an indicia indicating the location of the seal portion of the plunger relative to the aperture.

31. The medical device of claim 29, wherein the syringe further includes a plunger positioned in the barrel, the plunger including a seal portion and a collar, the barrel includes a ridge, the collar of the plunger abuts the ridge of the barrel when the seal portion of the plunger is substantially adjacent to the aperture.

32. The medical device of claim 27, wherein the inflating means includes a valve positioned to allow air into the body.

33. A method of changing the volume of a pliable body having a volume, the method including the steps of
   providing a medical device including a pressure generator cooperating with the pliable body to define a fluid system, and a valve positioned between the fluid system and a fluid region positioned outside of the fluid system,
   generating a pressure in the fluid system using the pressure generator to deflate the pliable body from an ambient position,
   inserting the pliable body into a patient passageway and operating the valve to expose the fluid system to the fluid region while the pressure generator is coupled to the fluid system to inflate the pliable body into engagement with the patient passageway.

34. The method of claim 33, the pressure generator being a syringe including a barrel having a wall including an aperture and a plunger positioned within the barrel and including a body portion and a seal portion, the seal portion and the aperture define the valve.

35. The method of claim 33, further comprising the step of operating the valve to substantially isolate the fluid system from the fluid region.

36. The method of claim 35, further comprising the step of generating a pressure in the fluid system using the pressure generator after the valve substantially isolates the fluid system from the fluid region.

37. The method of claim 36, the medical device further includes a second valve positioned to lie in the fluid system, the method further comprising the step of operating the second valve to substantially seal the pliable body from the pressure generation device and the step of removing the pressure generator from fluid communication with the pliable body after the step of generating the pressure after the valve substantially isolates the fluid system from the fluid region.

38. The method of claim 33, the medical device further includes a second valve positioned to lie in the fluid system, the method further comprising the step of operating the second valve to substantially seal the pliable body from the pressure generation device and the step of removing the pressure generator from fluid communication with the pliable body after generating a pressure.

* * * * *